United States Patent [19]

Almstedt et al.

[11] Patent Number: 5,661,008
[45] Date of Patent: Aug. 26, 1997

[54] RECOMBINANT HUMAN FACTOR VIII DERIVATIVES

[75] Inventors: Annelie B. Almstedt; Eva Maria Gray (Hellström), both of Stockholm; Peter Lind, Upsala; Catherine Ljung, Vällingby; Helena Inga Sandberg, Bromma; Jack Spira, Solna; Mona Sydow-Bäckman, Saltsjöbaden; Helena Wiman, Stockholm, all of Sweden

[73] Assignee: Kabi Pharmacia AB, Upsala, Sweden

[21] Appl. No.: 462,917

[22] Filed: Jun. 5, 1995

Related U.S. Application Data

[63] Continuation of Ser. No. 934,495, Dec. 17, 1992, abandoned.

[30] Foreign Application Priority Data

Mar. 15, 1991 [SE] Sweden .................... 9100799

[51] Int. Cl.$^6$ ............ C07K 14/755; C12N 5/10; C12N 15/12; C12N 15/63
[52] U.S. Cl. ............ 435/69.6; 435/172.3; 435/325; 435/320.1; 435/358; 530/383; 536/23.5
[58] Field of Search ............ 435/69.6, 320.1, 435/240.2, 172.3; 530/383; 930/100; 536/23.5

[56] References Cited

U.S. PATENT DOCUMENTS

| | | | |
|---|---|---|---|
| 4,769,326 | 9/1988 | Rutter | 435/68.1 |
| 4,868,112 | 9/1989 | Toole | 435/69.6 |

FOREIGN PATENT DOCUMENTS

| | | |
|---|---|---|
| 74868/87 | 12/1987 | Australia. |
| 1319628 | 6/1993 | Canada. |
| 0 212 532 | 4/1987 | European Pat. Off.. |
| 0 225 579 | 6/1987 | European Pat. Off.. |
| 0253455 | 1/1988 | European Pat. Off.. |
| 0295597 | 12/1988 | European Pat. Off.. |
| 0 303 540 | 2/1989 | European Pat. Off.. |
| 87/04187 | 7/1987 | WIPO. |
| 88/00831 | 5/1988 | WIPO. |

OTHER PUBLICATIONS

Proc. Natl. Acad. Sci. U.S.A., "Isolation and characterization of human factor VIII: Molecular forms in commercial factor VIII concentrate, cryoprecipitate, and plasma", vol. 83, pp. 2979 to 2983 (May 1986), L.O. Andersson et al.
Journal of Biological Chemistry, "The Functional Domains of Coagulation Factor VIII:C", vol. 261, No. 27, pp. 12574 to 12578 (1986), Rae Lyn Burke et al.
Biochemistry, vol. 25, No. 26 (Dec. 30, 1986), "Construction and Characterization of an Active Factor VIII Variant Lacking the Central One-Third of the Molecule", Dan L. Eaton, et al.
"Expression of Active Human Factor VIII From Recombinant DNA Clones", William I. Wood et al, Nature vol. 312, 22 Nov. 1984, pp. 330–337.
"Structure of Human Factor VIII", Gordon A. Vehar et al, Nature vol. 312, pp. 337–342 (1984).
"Purified Human Factor VIII Procoagulant Protein: Comparative Hemostatic Response After Infusions into Hemophilic and Von Willebrand Disease Dogs", K.M. Brinkhous et al, Proc. Natl. Acad. Sci. USA, vol. 82, pp. 8752–8756, Dec. 1985.
"A Large Region ( 95 kDa) of Human Factor VIII is Dispensable for In Vitro Procoagulant Activity", John J. Toole et al, Proc. Natl. Acad. Sci. UA, vol. 83, pp. 5939–5942, Aug. 1986.
"Stable Expression of Recombinant Factor VIII Molecules Using a Bovine Papillomavirus Vector", Nava Sarver et al, DNA, vol. 6, No. 6, 1987, pp. 553–564.
"Synthesis of Biologically Active Deletion Mutants of Human Factor VIII:C", K.D. Langner et al, Behring Inst. Mitt., No. 82, 16–25 (1988).
"A New Recombinant Procoagulant Protein Derived from the cDNA Encoding Human Factor VIII", Pierre Meulien et al, Protein Engineering, vol. 2, No. 4, pp. 301–306, 1988.
"Two Independent Domains of Factor VIII Co-Expressed Using Recombinant Vaccinia Viruses Have Procoagulant Activity", Andrea Pavirani et al, Biochemical and Biophysical Research Communications, vol. 145, No. 1, 1987, May 29, 1987, pp. 234–240.

*Primary Examiner*—Dian C. Jacobson
*Attorney, Agent, or Firm*—Burns, Doane, Swecker & Mathis, L.L.P.

[57] ABSTRACT

A DNA sequence coding for a biologically active recombinant human factor VIII derivative, comprising a first DNA segment coding for the amino acids 1 through 740 of human factor VIII and a second DNA segment coding for the amino acids 1649 through 2332 of human factor VIII, said segments being interconnected by a linker DNA segment coding for a linker peptide of at least 3 amino acid residues and up to about 10 amino acid residues which are selected from lysine and arginine; recombinant expression vector comprising such DNA sequence; host cells of animal origin transformed with such recombinant expression vector; a process for the manufacture of recombinant human factor VIII derivative; and human factor VIII derivative containing the heavy chain and the light chain linked by metal ion bond.

13 Claims, 8 Drawing Sheets

FIG.7
Thrombinactivation of rFVIII:R5

FIG.8

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

AACAATGCCA TTGAACCAAG AAGAAGAGAA ATAACTCGTA CTACTCTTCA G      51

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

ATTGAACCAA GAAGAAGAAG AGAAATAACT CGTACT      36

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

GATAACAATT TCACACA      17

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

AGTACGAGTT ATTTCTCTTC TTCTTCTTGG TTCAAT      36

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

```
GTAACGCCAG GGTTTTCC                                                                                                    18
```

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:6:

```
ATTGAACCAA GAAGAAGAAG AAGAGAAATA ACTCGTACT                                                                              39
```

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

```
AGTACGAGTT ATTTCTCTTC TTCTTCTTCT TGGTTCAAT                                                                              39
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:8:

```
Ile Glu Pro Arg Arg Arg Glu Ile Thr
 1               5
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:9:

```
Ile Glu Pro Arg Arg Arg Arg Glu Ile Thr
 1               5                   10
```

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:10:

```
Ile Glu Pro Arg Arg Arg Arg Arg Glu Ile Thr
 1               5                       10
```

RECOMBINANT HUMAN FACTOR VIII DERIVATIVES

This application is a continuation of application Ser. No. 07/934,495, filed Dec. 17, 1992 now abandoned.

The present invention relates to DNA sequences coding for biologically active recombinant human factor VIII derivatives, recombinant expression vectors containing such DNA sequences, host cells transformed with such recombinant expression vectors, and processes for the manufacture of the recombinant human factor VIII derivatives. The invention also covers human factor VIII derivatives comprising two polypeptides linked by a metal ion bridge.

BACKGROUND OF THE INVENTION

Classic hemophilia or hemophilia A is the most common of the inherited bleeding disorders. It results from a chromosome X-linked deficiency of blood coagulation factor VIII, and affects almost exclusively males with an incidence of between one and two individuals per 10 000. The X-chromosome defect is transmitted by female carriers who are not themselves hemophiliacs. The clinical manifestation of hemophilia A is an abnormal bleeding tendency and before treatment with factor VIII concentrates was introduced the mean life span for a person with severe hemophilia was less than 20 years. The use of concentrates of factor VIII from plasma has considerably improved the situation for the hemophilia patients. The mean life span has increased extensively, giving most of them the possibility to live a more or less normal life. However, there have been certain problems with the plasma derived concentrates and their use, the most serious of which have been the transmission of viruses. So far, viruses causing AIDS, hepatitis B, and non A non B hepatitis have hit the population seriously. Although different virus inactivation methods and new highly purified factor VIII concentrates have recently been developed no guarantees on the absence of virus contamination can be made. Also, the factor VIII concentrates are fairly expensive because the limited supply of human plasma raw material.

A factor VIII product derived from recombinant material is likely to solve a large extent of the problems associated with the use of plasma derived factor VIII concentrates for treatment for hemophilia A, and a number of groups are presently working on the development of such a product. However, the development of of a recombinant factor VIII have met with some difficulties, for instance the problem of achieving production levels in sufficiently high yields, in particular regarding the full-length molecule.

In fresh plasma prepared in the presence of protease inhibitors, factor VIII has been shown to have a molecular weight of 280 kDa and to be composed of two polypeptide chains of 200 kDa and 80 kDa, respectively (Andersson. L.-O., et al. (1986) Proc. Natl. Acad. Sci. U.S.A. 83, 2979–2983). These chains are held together by metal ion bridges. More or less proteolytically degraded forms of the factor VIII molecule can be found as active fragments in factor VIII material purified from commercial concentrates (Andersson, L.-O., et al, ibid.; Andersson, L.-O., et al (1985) EP 0197901). The fragmented form of factor VIII having molecular weights from 260 kDa down to 170 kDa, consists of one heavy chain with a molecular weight ranging from 180 kDa down to 90 kDa, where all variants have identical amino termini, in combination with one 80 kDa light chain. The amino-terminal region of the heavy chain is identical to that of the single chain factor VIII polypeptide that can be deduced from the nucleotide sequence data of the factor VIII cDNA (Wood, W. I., et al. (1984) Nature 312, 330–336; Vehar, G. A., et al. (1984) Nature 312, 337–342).

The smallest active form of factor VIII with a molecular weight of 170 kDa, consisting of one 90 kDa and one 80 kDa chain, can be activated with thrombin to the same extent as the higher molecular weight forms, and thus represents an unactivated form. It has also been shown to have full biological activity in vivo as tested in hemophilia dogs (Brinkhous, K. M., et al. (1985) Proc. Natl. Acad. Sci. U.S.A. 82, 8752–8756). Thus, the haemostatic effectiveness of the 170 kDa form is the same as for the high molecular weight forms of factor VIII.

The fact that the middle heavily glycosylated region of the factor VIII polypeptide chain residing between amino acids Arg-740 and Glu-1649 does not seem to be necessary for full biological activity has prompted several researchers to attempt to produce derivatives of recombinant factor VIII lacking this region. This has been achieved by deleting a portion of the cDNA encoding the middle heavily glycosylated region of factor VIII either entirely or partially.

For example, J. J. Toole, et al. reported the construction and expression of Factor VIII lacking amino acids 982 through 1562, and 760 through 1639 respectively (Proc. Natl. Acad. Sci. U.S.A. (1986) 83, 5939–5942). D. L. Eaton, et al. reported the construction and expression of Factor VIII lacking amino acids 797 1 through 1562 (Biochemistry (1986) 25, 8343–8347). R. J. Kaufman described the expression of Factor VIII lacking amino acids 741 through 1646 (PCT application No. WO 87/04187). N. Sarver, et al. reported the construction and expression of Factor VIII lacking amino acids 747 through 1560 (DNA (1987) 6, 553–564). M. Pasek reported the construction and expression of Factor VIII lacking amino acids 745 through 1562, and amino acids 741 through 1648, respectively (PCT application No.88/00831). K.-D. Lagner reported the construction and expression of factor VIII lacking amino acids 816 through 1598, and amino acids 741 through 1689, respectively (Behring Inst. Mitt., (1988) No 82, 16–25, EP 295597). P. Meulien, et al., reported the construction and expression of factor VIII lacking amino acids 868 through 1562, and amino acids 771 through 1666, respectively (Protein Engineering (1988) 2(4), 301–306, EPO 303 540 A1). When expressing these deleted forms of Factor VIII cDNA in mammalian cells the production level is typically 10 times higher as compared to full-length Factor VIII.

Furthermore, attempts have been made to express the 90 kDa and 80 kDa chains separately from two different cDNA derivatives in the same cell (Burke, R. L., et al (1986), J. Biol. Chem. 261, 12574–12578, Pavirani, A., et al. (1987) Biochem. Biophys. Res. Comm., 145, 234–240). However, in this system the in vivo reconstitution seems to be of limited efficiency in terms of recovered Factor VIII:C activity.

This invention describes deleted factor VIII cDNA molecules that code for recombinant factor VIII derivatives, corresponding, as regards to molecular weight and other biochemical characteristics, to a previously derived plasma factor VIII form present in considerable amounts in commercial concentrates (Andersson, L.-O. et al (1986), Proc. Natl. Acad. Sci. U.S.A. 83, 2979–2983). These new deleted factor VIII cDNA derivatives are likely to give sufficiently high yields of recombinant factor VIII protein to be used in an industrial process for a pharmaceutical preparation of recombinant factor VIII.

DEFINITIONS USED

In the following sections, the term "factor VIII deletion derivative" is defined as one or more polypeptide chains having factor VIII:C activity derived from the 2332 amino acid full-length factor factor VIII polypeptide by deleting a segment comprising the amino acids 741 through 1648, and replacing said segment by a linker segment consisting of at least three basic amino acids, i.e. selected from lysine and arginine. The term "factor VIII:RE" is defined as a polypeptide chain derived from full-length factor VIII lacking amino acids 741 through 1648. The term "factor VIII:QD" is defined as a polypeptide chain derived from full-length factor VIII lacking amino acids 745 through 1562. The term "factor VIII:R3" is defined as a polypeptide lacking amino acids 741 through 1648 with said segment replaced by two arginine residues. The term "factor VIII:R4" is defined as a polypeptide lacking amino acids 741 through 1648 with said segment replaced by three arginine residues. The term "factor VIII:R5" is defined as a polypeptide lacking amino acids 741 through 1648 with said segment replaced by four arginine residues.

DESCRIPTION OF THE INVENTION

The present invention deals with techniques for the production of proteins having factor VIII:C activity. More specifically, the present invention provides modified factor VIII cDNA sequences, derived from the full-length factor VIII cDNA, that upon expression in animal cells give rise to high level production of proteins with factor VIII:C activity consisting essentially of two polypeptide chains having 90 kDa and 80 kDa molecular wight, respectively.

Accordingly, the present invention provides for a DNA sequence encoding a biologically active recombinant human factor VIII derivative, comprising a first DNA segment coding for the 90 kDa chain of human factor VIII and a second DNA segment coding for the 80 kDa chain of human factor VIII, said segment being interconnected by a linker DNA segment encoding a linker peptide of at least 2 amino acid residues selected from lysine and arginine.

Although the length of the linker peptide coded for by said linker DNA segment is not critical it is preferred that it does not contain more than about 10 amino acid residues.

It is particularly preferred that the linker peptide is constituted by 2, 3 or 4 amino acid residues, particularly 3 or 4 amino acid residues. It is especially preferred that the amino acid residue preceding Glu-1649 is constituted by arginine.

In accordance with the present invention it is preferred that all amino acid residues forming the linker peptide are arginine residues.

It is to be noted that the linker peptide is built up from basic amino acids, namely lysine and/or arginine residues. Among these two arginine residues are preferred.

The invention also relates to a recombinant expression vector containing a transcription unit comprising the DNA sequence as outlined above and, furthermore, a promoter and a polyadenylation signal sequence.

The invention also covers host cells of animal origin transformed with the recombinant expression vector as defined above.

Additionally, the invention provides for a process for the manufacture of a biologically active recombinant human factor VIII derivative as described above, said process comprising cultivating an animal cell line transformed with a recombinant expression vector as defined above in a nutrient medium allowing expression and secretion of a human factor VIII derivative composed of the 90 kDa domain and, linked thereto by a metal ion bond, the 80 kDa domain, said expressed derivative being then recovered from the culture medium.

Finally, the invention provides for a human factor VIII derivative comprising the 90 kDa chain and, linked thereto, optionally via the linker peptide or part thereof, by a metal ion bond, the 80 kDa chain of human factor VIII.

In order to obtain a protein with factor VIII:C activity consisting of the above polypeptide chains, the single polypeptide chain created during translation in vivo has to be cleaved either by post-translational processing during the biosynthetic process in the producing cell or by proteolytic processing in vitro, or both. Since a protein with factor VIII:C activity, consisting of two polypeptide chains of 200 kDa and 80 kDa molecular weight, can be isolated from human plasma, it is assumed that there exists an appropriate cleavage site for processing enzymes on the single chain full-length factor VIII primary translation product. An important in vivo processing site is most probably located at the carboxy-terminal side of Arg-1648. During proteolytic maturation, cleavage at Arg-1648 gives rise to a factor VIII protein consisting of the above chains of 200 kDa and 80 kDa molecular weight. Since Arg-1648 seems to be located at a border between structural domains in the factor VIII molecule, it may constitute a sterically accessible target for the processing enzyme or enzymes. Another processing site may exist at Arg-740 which will give rise to the conversion of the 200 kDa chain to a 90 kDa chain in vitro, thus giving rise to the 90 kDa and 80 kDa form of factor VIII present in commercial human plasma derived factor VIII concentrates. In accordance with the present invention it has been found that in order to produce factor VIII deletion derivatives that can be processed, either in vivo or in vitro, to proteins consisting of two polypeptide chains of 90 kDa and 80 kDa molecular weight, the 908 amino acid polypeptide chain interconnecting Arg-740 and Glu-1649 in the full-length factor VIII protein, can be replaced by at least three basic amino acid residues, that is lysine or arginine residues or both. Preferably, the amino acid at the amino-terminal side of Glu-1649 should be an arginine residue.

The production of factor VIII proteins consisting of two polypeptide chains according to the above at high levels in suitable host cells, requires the assembly of the factor VIII deletion derivative cDNA:s into efficient transcriptional units together with suitable regulatory elements in a cloning vector, that can be propagated in E. coli according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the factor VIII cDNA:s, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The factor VIII cDNA:s thus assembled into efficient transcriptional units are then introduced into a suitable host organism for expression of the different factor VIII proteins. Preferably this organism should be an animal cell-line of vertebrate origin in order to ensure correct folding, disulfide bond formation, asparagine-linked glycosylation and other post-translational modifications as well as secretion into the cultivation medium. Examples on other post-translational modifications are tyrosine O-sulfatation, and proteolytic processing of the nascent polypeptide chain essential to the formation of the 90 kDa and 80 kDa two chain factor VIII molecules. Examples of cell-lines that can be use are monkey COS-cells, mouse L-cells, mouse C127-cells, hamster BHK-21 cells, human embryonic kidney 293 cells, and preferentially CHO-cells.

The transcription units encoding the factor VIII cDNA:s can be introduced into an animal cell-line in several different ways. For instance, recombinants can be created the above transcription units and vectors based on different animal viruses. Examples of these are vectors based on baculovirus, vaccinia virus, adenovirus, and preferrably bovine papilloma virus.

The transcription units encoding the factor VIII cDNA:s can also be introduced into animal cells together with another recombinant gene which may function as a dominant selectable marker in these cells in order to facilitate the isolation of specific cell clones which have integrated the recombinant DNA into their genome. Examples of this type dominant selectable marker genes are Tn5 aminoglycoside phosphotransferase, conferring resistance to Geneticin (G418), hygromycin phosphotransferase, conferring resistance to hygromycin, and puromycin acetyl transferase, conferring resistance to puromycin. The transcriptional unit encoding such a selectable marker can reside either on the same vector as the one encoding the factor VIII cDNA, or it can be encoded on a separate vector which is simultaneously introduced and integrated to the genome of the host cell, frequently resulting in a tight physical linkage between the different transcription units.

Other types of selectable marker genes which can be used together with the factor VIII cDNA:s are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthin, thymidin, and glycin. These dhfr-genes can be introduced together with the factor VIII cDNA transcriptional units into CHO-cells of the above type, either linked on the same vector or on different vectors, thus creating dhfr-positive cell-lines producing recombinant factor VIII protein.

If the above cell-lines are grown in the presence of the cytotoxic dhfr-inhibitor methotrexate, new cell-lines resistant to methotrexate will emerge. These cell-lines may produce recombinant factor VIII protein at an increased rate due to the amplified number of linked dhfr and factor VIII transcriptional units. When propagating these cell-lines in increasing concentrations of methotrexate (1–10000 nM), new cell-lines can be obtained which produce factor VIII protein at very high rate.

The above cell-lines producing factor VIII protein can be grown on a large scale, either in suspension culture or on various solid supports. Examples of these supports are microcarriers based on dextran or collagen matrices, or solid supports in the form of hollow fibers or various ceramic materials. When grown in suspension culture or on microcarriers the culture of the above cell-lines can be performed either as a batch culture or as a perfusion culture with continuous production of conditioned medium over extended periods of time. Thus, according to the present invention, the above cell-lines are well suited for the development of an industrial process for the production of recombinant factor VIII which corresponds to the authentic two polypeptide chain Factor VIII (90 kDa and 80 kDa) that can be isolated from human plasma.

The recombinant factor VIII protein which accumulate in the medium of CHO-cells of the above type, can be concentrated and purified by a variety of biochemical methods, including methods utilizing differences in size, charge, hydrophobicity, solubility, specific affinity, etc. between the recombinant factor VIII protein and other substances in the cell cultivation medium.

An example of such a purification is the adsorption of the recombinant factor VIII protein to a monoclonal antibody which is immobilised on a solid support. After desorption, the factor VIII protein can be further purified by a variety of chromatographic techniques based on the above properties.

The recombinant proteins with factor VIII activity described in this invention can be formulated into pharmaceutical preparations for therapeutic use. The purified factor VIII proteins may be dissolved in conventional physiologically compatible aqueous buffer solutions to which there may be added, optionally, pharmaceutical adjuvants to provide pharmaceutical preparations.

The present invention will be further described more in detail in the following by non-limiting examples thereof. This description of specific embodiments of the invention will be made in conjunction with the appended drawings, wherein:

FIG. 3);

EXAMPLE 1

A series of deletion derivatives of factor VIII cDNA have been constructed that encode polypeptide chains devoid of all of the B-domain, but containing different numbers of basic amino acids linking the carboxy-terminus of the heavy chain to the amino-terminus of the light chain. These factor VIII deletion derivatives are subject to in vivo proteolytic processing of the primary translation product into two polypeptide chains. In the examples given below the amino acid nomenclature refers to the positions given in the full-length factor VIII molecule without the signal sequence. Mutagenesis of factor VIII cDNA to create the factor VIII:R3 deletion, A 627 base-pair KpnI-PstI restriction fragment obtained from the cDNA of a factor VIII deletion derivative (factor VIII:RE, M. Pasek, PCT application No. WO88/00831, ATCC 53517) encoding the amino acids Leu 587 through Ala 1702 linked via a direct fusion between Arg 740 and Glu 1649 of full-length factor VIII, was introduced into the bacteriophage vector M13mp19 (Yanisch-Perron, C. et al. (1985) Gene 33, 103–119) according to standard methods. Oligonucleotide directed mutagenesis (Nakamaye, K. and Eckstein, F. (1986) Nucleic Acids. Res. 14, 9679–9698) was performed on single stranded DNA template prepared from the above recombinant bacteriophage. 10 μg purified circular single stranded phage DNA was annealed to 8 pmoles of a 5'-phosphorylated oligonucleotide of the sequence [SEQ ID NO:1]:

5'-AACAATGCCATTGAACCAAGAAGAAGAGAAATAACTCGTACTACTCTTCAG-3'

The second strand of circular DNA was synthesised on the resulting template by addition of all four deoxynucleotides, dCTPαS, 12 units of the Klenow fragment of DNA-polymerase 1, and 12 units of T4 DNA-ligase. After overnight incubation at 16° C., the reaction mixture was enriched for double stranded DNA by filtering through nitrocellulose in the presence of 500 mM NaCl. One fifth of the purified double stranded DNA was nicked by incubation with 5 units of the restriction enzyme NciI, treated by 50 units of Exonuclease III to such an extent that the template strand of the phage DNA was partially removed. The resulting partial duplex was rendered double stranded by treatment with 3 units of DNA polymerase 1 and 2 units T4 DNA-ligase in the presence of all four deoxynucleotide triphosphates at 16° C. for 3 hours. One fourth of the resulting mixture was used to transform 300 μl competent E. coli TG1. Of the resulting mutagenised phage clones, ten were subjected to dideoxy DNA sequencing (Sanger, F. et al. (1977) Proc. Natl. Acad. Sci. U.S.A. 74, 5463–5467). One of the sequenced phage clones contained an insert with the expected nucleotide sequence dictated by the above mutagenic primer. Thus, the phage insert consists of a 630 base-pair KpnI-PstI fragment of the factor VIII cDNA encoding a fusion between Arg 740 and Glu 1649 via two extra Arg residues (factor VIII:R3). Construction of a Mammalian Expression Vector Encoding factor VIII:R3.

Figure 1:
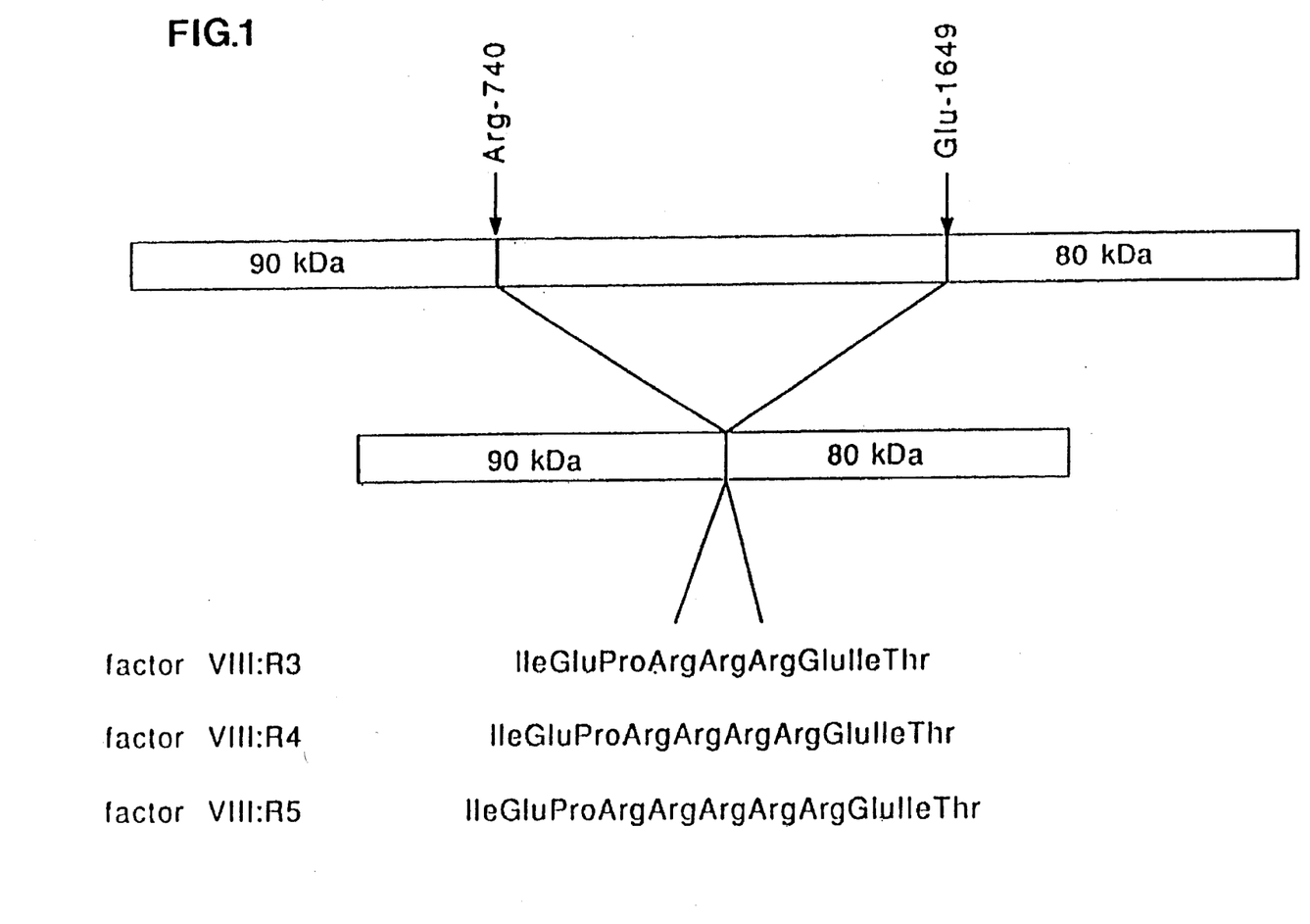
FIG. 1 is a schematic representation of the relationship between full-length factor VIII and factor VIII:R3 [SEQ ID NO:8], factor VIII:R4 [SEQ ID NO:9], and factor VIII:R5 [SEQ ID NO:10], respectively. The primary structure of the region between C-terminus of the 90 kDa chain (Arg-740) and the N-terminus of the 80 kDa chain (Glu-1649) is shown.
Figure 2:
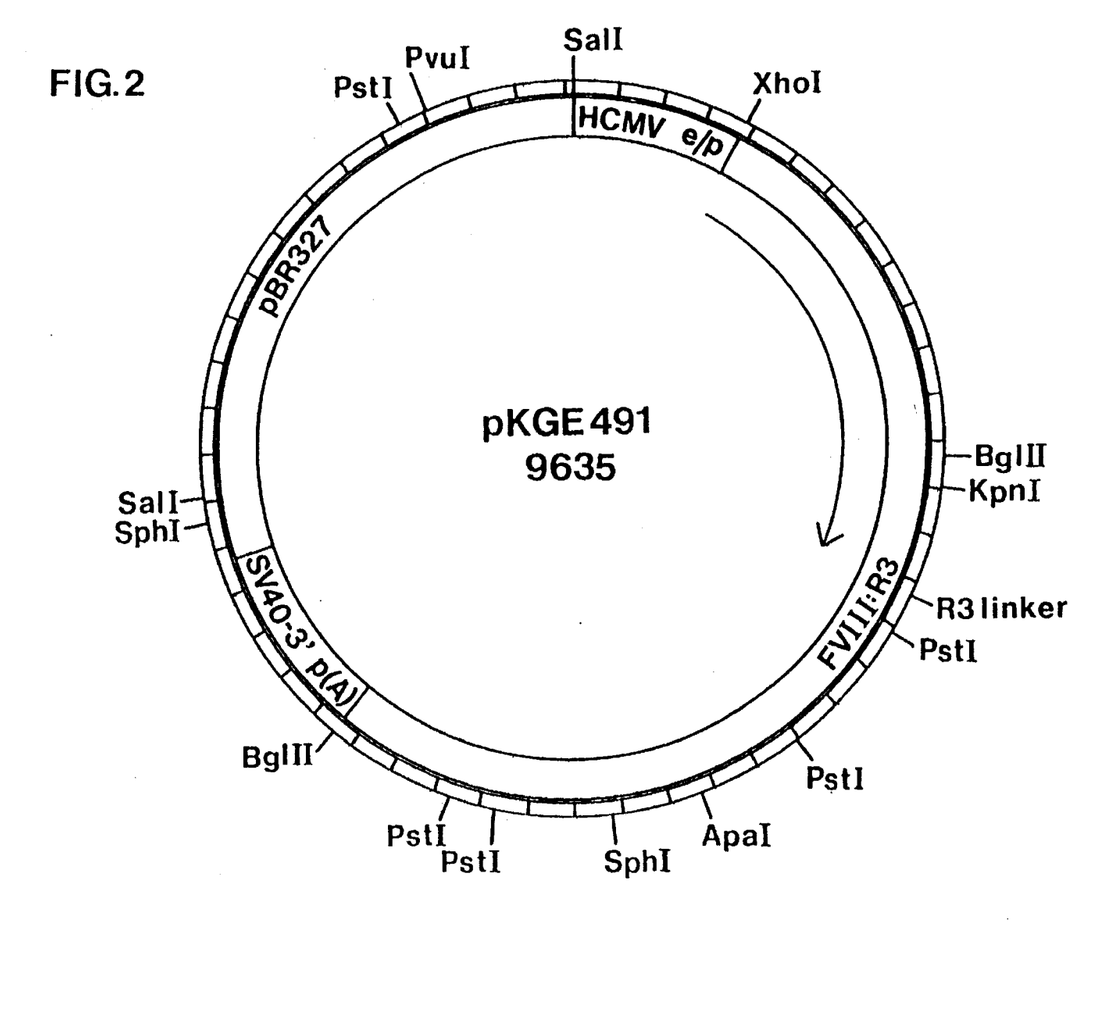
FIG. 2 is an illustration of the plasmid pKGE491 containing the factor VIII:R3 cDNA under transcriptional control of the human cytomegalovirus promoter.

The 630 base-pair KpnI-PstI fragment encoding the factor VIII:R3 fusion according to the above was excised from the double stranded replicative form of the M13mp19 phage DNA and introduced to the vector pKGE431. This vector consists of a 2046 base-pair KpnI-SphI fragment from the factor VIII:RE cDNA (M. Pasek, PCT application No. WO88/00831, ATCC 53517) encoding amino acids Leu 587 through Met 2176 of the factor VIII:RE protein in pUC19. The 630 base-pair fragment encoding the factor VIII:R3 fusion according to the above was introduced into pKGE431 that had been completely cleaved by KpnI and partially cleaved by PstI. The resulting vector, pKGE490, contains a 2052 base-pair KpnI-SphI insert encoding the amino acids Leu 587 through Met 2176 of factor VIII:R3. pKGE490 was digested with KpnI and ApaI and the corresponding 1665 base-pair fragment encoding Leu 587 through Ala 2047 of the factor VIII:R3 protein was ligated to the large fragment of the vector pKGE347 that had been digested with KpnI and ApaI. The vector pKGE347, which is based on the E. coli cloning vector pBR327, consists of the human cytomegalovirus enhancer/promoter encoded on a 741 base-pair DNA-segment (nucleotide positions −671 to +71, Boshart, M. et al. (1985) Cell 41,521–530) upstream of the Factor VII:QD cDNA with the SV40 t-antigen intron and polyadenylation sequence at the 3'-proximal part. The resulting vector (pKGE491), which is depicted in FIG. 2, contains the complete factor VIII:R3 cDNA and is identical to pKGE347 except for the different deletion derivative of factor VIII that is encoded.

Mutagenesis of factor VIII cDNA to create the factor VIII:R4 deletion.

The 630 base-pair KpnI-Pst fragment encoding part of the factor VIII:R3 cDNA according to the above was introduced into the vector pUC19 that had been opened by the same enzymes. The resulting vector, denoted pKGE657, was then subject to site-directed mutagenesis by overlap extension using the polymerase chain reaction (Ho, S. N., et al. (1989) Gene 77, 51–59; Saiki, R. K. et al. (1988) Science 239, 487–491). In the first part of the mutagenesis reaction, two parallel experiments were set up. In experiment number one, 100 ng of the plasmid pKGE657 was mixed with 1 μM each of the following two primers [SEQ ID NOS: 2 and 3]:

5'-ATTGAACCAAGAAGAAGAAGAGAAATAACTCGTACT-3'

5'-GATAACAATTTCACACA-3'

To this, in a final reaction volume of 100 μl, were added, 50 mM KCl, 10 mM Tris-HCl pH 8.3, 1.5 mM MgCl$_2$, 0.01% gelatin, 200 μM each of the four deoxynucleotides, and 2.5 units of Taq polymerase. The samples were subjected to 25 cycles of denaturation at 94° C. for 1 min., annealing at 50° C. for 2 min., and extension at 72° C. for 3 min., using a DNA Thermal Cycler according to the specifications of the manufacturer (Perkin Elmer Cetus). Analysis of the reaction products with agarose gel electrophoresis and staining with ethidium bromide according to standard procedures, indicated the formation of a single amplified DNA product with the length of 240 base-pairs. In experiment number two, the polymerase chain reaction was performed in an identical manner using the following two primers [SEQ ID NOS. 4 and 5]:

5'-AGTACGAGTTATTTCTCTTCTTCTTCTTCTTGGTTCAAT-3'

5'-GTAACGCCAGGGTTTTCC-3'

Analysis of the reaction products with agarose gel electrophoresis indicated the formation of a single amplified DNA product with the length of 550 base-pairs. In the second part of the mutagenesis 10 μl each of the product mixtures from the two above parallel experiments were combined in a third polymerase chain reaction in a total volume of 100 μl, with conditions identical to the above, except that only the following two primers [SEQ ID NOS. 5 and 3] were used:

5'-GTAACGCCAGGGTTTTCC-3'

5'-GATAACAATTTCACACA-3'

Analysis of the reaction mixture with agarose gel electrophoresis indicated the formation of a single amplified DNA product with the length of 750 base-pairs. This DNA fragment was digested with Kpnl and Pstl and introduced into the vector pUC19 opened with the same enzymes. Several of the resulting plasmids were DNA sequenced with the dideoxy chain termination method (Sanger, F., et al., vide supra), and a plasmid with the expected 633 base-pair Kpnl-Pst fragment with correct sequence was denoted pKGE658. Thus, this plasmid insert consists of a fragment of factor VIII:R4 cDNA encoding a fusion between Arg 740 and Glu 1649 via three extra Arg residues.

Construction of a Mammalian Expression Vector Encoding factor VIII:R4.

Figure 3:
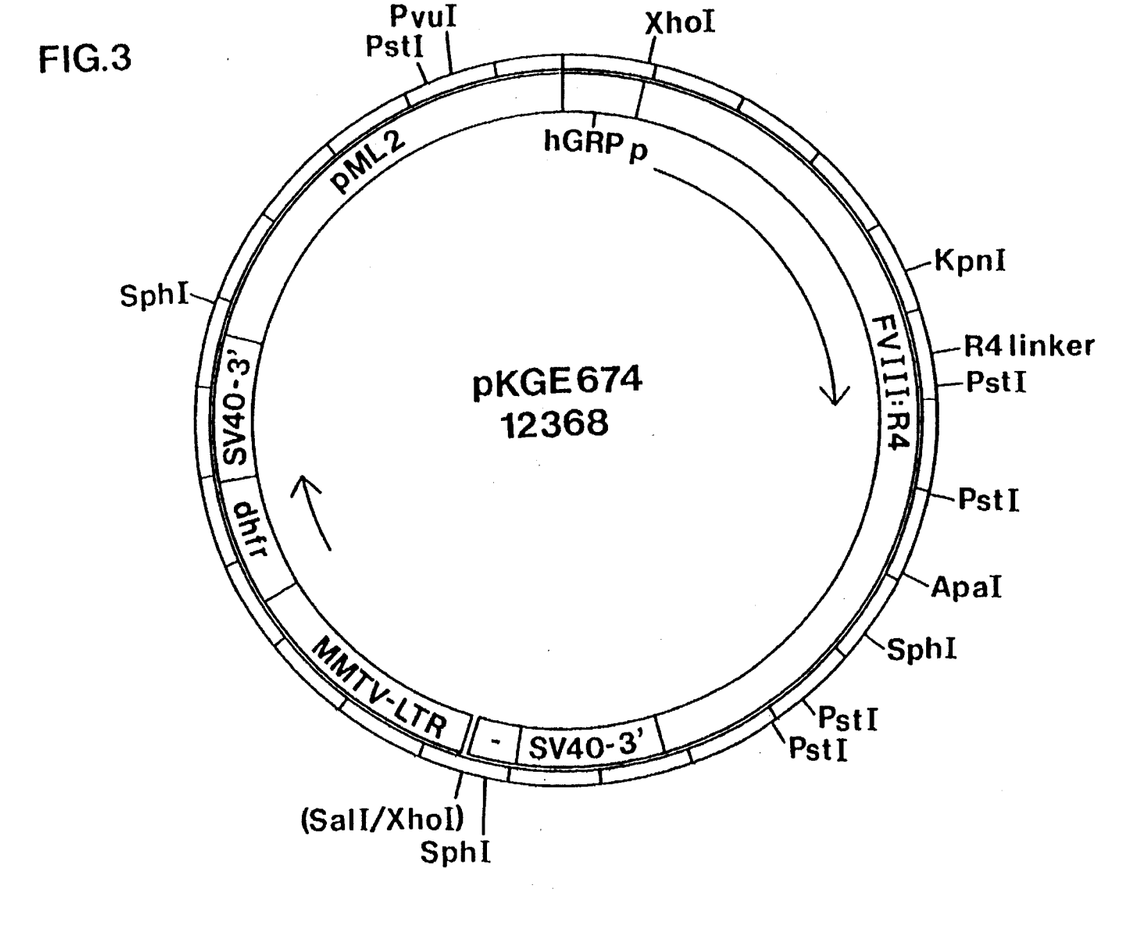
FIG. 3 is an illustration of the plasmid pKGE674 containing the factor VIII:R4 cDNA under transcriptional control of the human GRP78 promoter, and an additional transcriptional unit encoding the mouse dihydrofolate reductase cDNA under transcriptional control of the mouse mammary tumor virus long terminal repeat.

The 633 base-pair Kpnl-Pstl fragment encoding part of the factor VIII:R4 cDNA was excised from the vector pKGE658 and introduced to the vector pKGE490 that had been completely cleaved by Kpnl and partially cleaved by Pstl. The resulting vector, pKGE673, contains a 2055 base-pair Kpnl-Sphl insert encoding amino acids Leu 587 through Met 2176 of factor VIII:R4. A 1668 base-pair Kpnl-Apal fragment encoding Leu 587 through Ala 2047 of the factor VIII:R4 was excised from pKGE673 and transferred to the large fragment of the vector pKGE601 that had been opened with the same enzymes. The vector pKGE601, which is based on the E. coli cloning vector pML2, consists of the human GRP78 enhancer/promoter encoded on a 443 base-pair DNA-segment (nucleotide positions 2 to 445, Ting, J. & Lee, A. S. (1988) DNA 7(4), 275–286) upstream of the factor VIII:R5 cDNA with the SV40 t-antigen intron and polyadenylation sequence at the 3'-proximal region. Placed downstream of this region is a transcription unit encoding the mouse dihydrofolate reductase cDNA under control of the mouse mammary tumor virus long terminal repeat, and utilizing the same SV40 3' control element as above. The resulting vector, pKGE674, is depicted in FIG. 3.

Mutagenesis of factor VIII cDNA to create the factor VIII:R5 deletion.

The vector pKGE657 was subjected to site-directed mutagenesis by overlap extension using the polymerase chain reaction in a manner analogous to the above example regarding factor VIII:R4. As primers [SEQ ID NOS. 6 and 3] in the first of the two parallel reactions the following were used:

5'-ATTGAACCAAGAAGAAGAAGAAGAGAAATAACTCGTACT-3'

5'-GATAACAATTTCACACA-3'

Analysis of the reaction products with agarose gel electrophoresis, as in the above example, indicated the formation of a reaction product of 240 base-pairs. In the second of the two parallel reactions the following primers [SEQ ID NOS. 7 and 5] were used:

5'-AGTACGAGTTATTTCTCTTCTTCTTCTTCTTGGTTCAAT-3'

5'-GTAACGCCAGGGTTTTCC-3'

Analysis of the reaction products with agarose gel electrophoresis, indicated a reaction product of 550 base-pairs. The second part of the mutagenesis experiment, analogous to the above example, yielded an amplified DNA product of 760 base pairs. After digestion of this DNA with Kpnl and Pstl it was introduced into pKGE490 that had been completely cleaved by Kpnl and partially cleaved by Pstl.

A plasmid with the expected 636 base-pair Kpnl-Pst fragment of correct sequence as determined by the dideoxy chain termination method (Sanger, F., et al., vide supra) was denoted pKGE659, and in total contains a 2058 base-pair Kpnl-Sphl insert consisting of a fragment of factor VIII:R5 cDNA that encodes a fusion between Arg-740 and Glu-1649 via four extra Arg residues.

Construction of a Mammalian Expression Vector Encoding factor VIII:R5.

Figure 4:
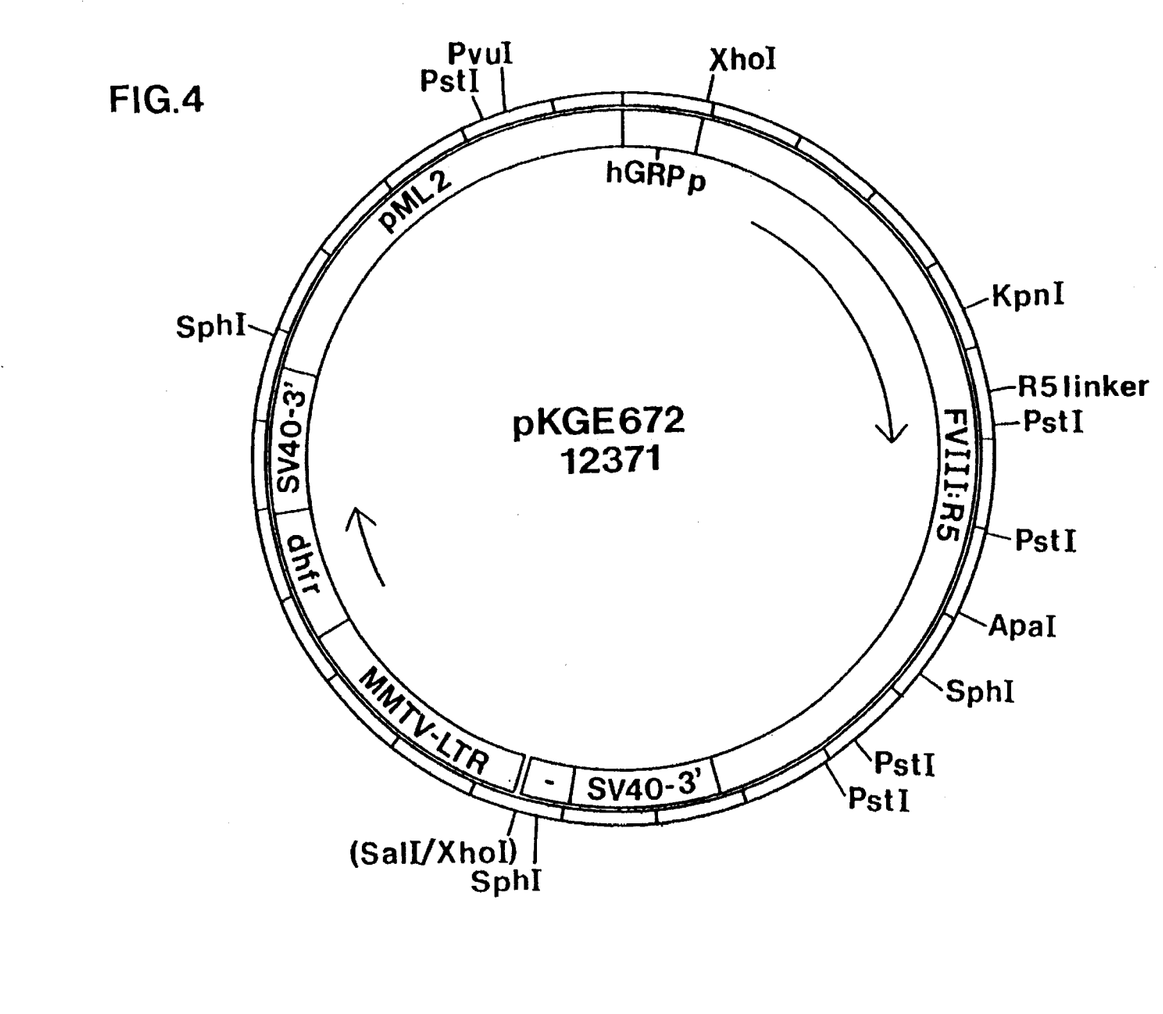
FIG. 4 is an illustration of the plasmid pKGE672 containing the factor VIII:R5 cDNA under the transcriptional control of the human GRP78 promoter, and the mouse dihydrofolate reductase similar o the vector depicted in FIG. 3.

A 1668 base-pair Kpnl-Apal fragment encoding Leu 587 through Ala 2047 of the factor VIII:R5 was excised from pKGE659 and transferred to the large fragment of the vector pKGE601 that had been opened with the same enzymes, in a manner similar to that described above for the factor VIII:R4 expression vector pKGE674. The resulting vector encoding factor VIII:R5 (pKGE672) is depicted in FIG. 4.

EXAMPLE 2

Derivation of Chinese Hamster Ovary Cells Producing factor VIII:R3.

Figure 5:
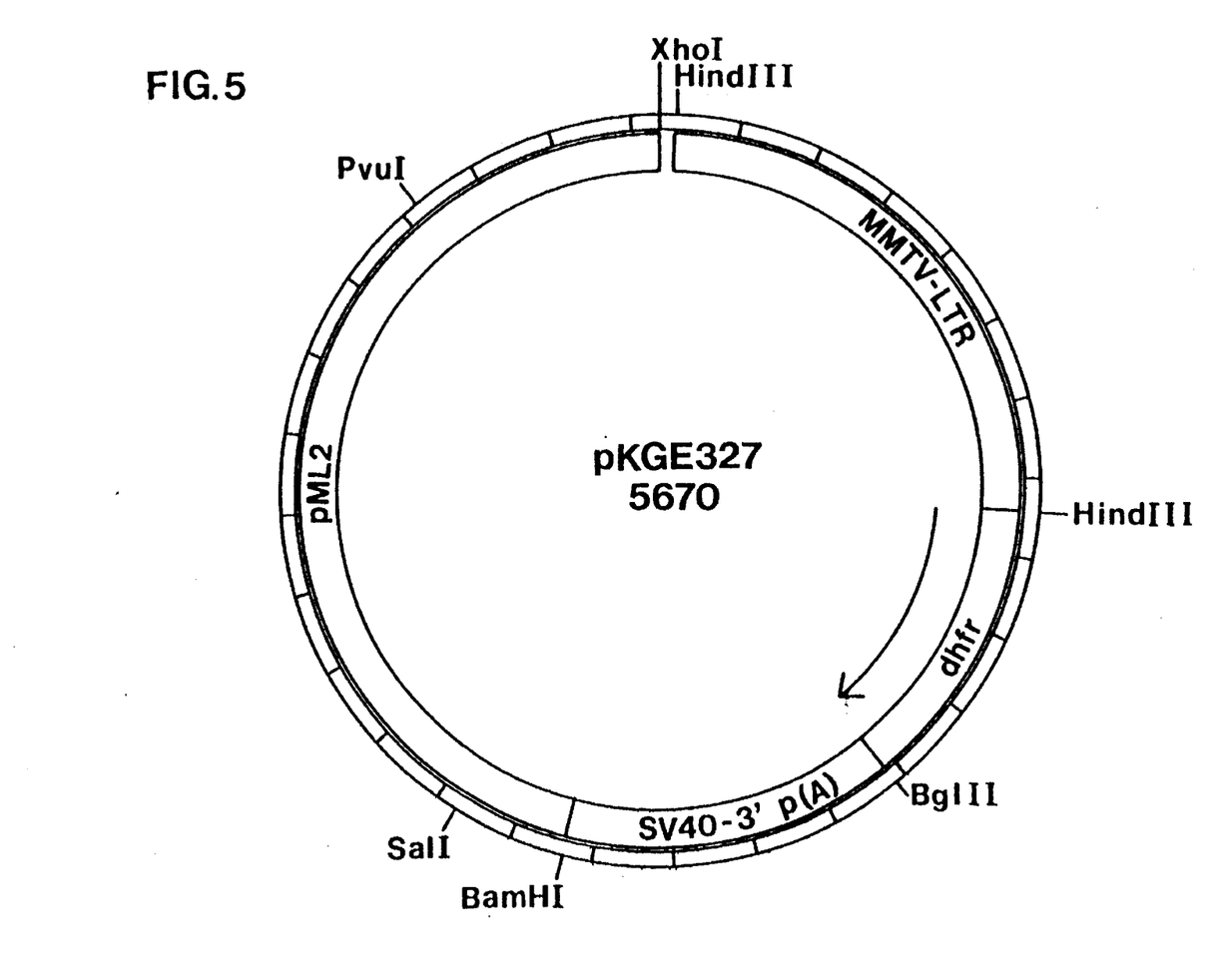
FIG. 5 is an illustration of the the plasmid pKGE327 containing only the mouse dihydrofolate reductase cDNA transcriptional unit (c.f.

In a 10 centimeter diameter cell culture dish, 0.5 million dihydro-folate reductase deficient Chinese Hamster Ovary Cells (CHO-DG44, Obtained from Dr L. A. Chasin, Columbia University, New York) were seeded in Dulbecco's Modified Eagles Medium/Ham's F12 (1:1) supplemented by 10% foetal calf serum and incubated over night at 37° C. in a 5% carbon dioxide incubator. The next day the cells were washed with fresh medium and subsequently transfected by the calcium phosphate method with 10 ug of a 1:1 mixture of the factor VIII:R3 expression vector PKGE491 and the dihydrofolate reductase vector pKGE327 according to the methods of the art. The vector pKGE327 contains a transcription unit consisting of the mouse mammary tumor virus long terminal repeat upstream of the mouse dihydrofolate reductase cDNA with the SV40 t-antigen and polyadenylation sequence at the 3'-proximal part cloned into the vector pML2 in a clockwise manner (FIG. 5). On day three, the medium was removed, the cells washed and split into new cell cultivation dishes. On day four, the selection for dihydrofolate reductase positive cells was initiated by replacing the medium with the above cell cultivation medium lacking hypoxanthin, glycin, and thymidin and supplemented with 10% thoroughly dialyzed foetal calf serum. The medium was changed twice a week and after approximately two weeks colonies of dihydrofolate reductase positive cells could be harvested. These colonies were pooled and further grown in 25 $cm^2$ cell culture bottles, and after reaching subconfluency the medium was replaced with fresh medium containing 3% foetal calf serum. After a period of 24 hours the activity of the Factor VIII:C in the culture medium was tested using the synthetic substrate method (Coatest Factor VIII:C, KABl-Pharmacia) and an expression level of 80 mU/ml was obtained. The pool of dihydrofolate reductase positive cells was subject to gene amplification by several weeks of cultivation in medium containing the dihyfrofolate reductase inhibitor methotrexate. After selection by stepwise increments of the concentration of methotrexate up to 500 nM, a pool of resistant cells were obtained that produced factor VIII:C at a level of 1.0 U/ml in roller bottles.

Derivation of Chinese Hamster Ovary Cells producing factor VIII:R4.

In a manner similar to the above transfection of the factor VIII:R3 encoding expression vector. Chinese Hamster Ovary. Cells were transfected with the factor VIII:R4 encoding expression vector pKGE674. In this case, co-transfection with the pKGE327 was omitted, since a transcription unit encoding the selection and amplification marker dihydrofolate reductase is present on this vector. After selection in medium lacking hypoxanthin, glycin, and thymidin and supplemented with 10% thoroughly dialyzed foetal calf serum similar to the above, a pool of cell clones was obtained that produced 400 mU/ml factor VIII:C activity as measured by the Coatest method. Selection for gene amplification by cultivation in 20 nM methotrexate for several weeks yielded a pool of cells that produced 500 mU/ml factor VIII:C. Further selection by cultivation in medium containing 200 nM methotrexate yielded a pool of cells that produced 980 mU/ml factor VIII:C. These cells, when cultivated in roller bottles, produced 800 mU/ml factor VIII:C.

Derivation of Chinese Hamster Ovary Cells Producing factor VIII:R5.

Similar to the above, Chinese Hamster Ovary Cells were transfected with the factor VIII:R5 encoding expression vector pKGE672, which encodes both the factor VIII:R5, and dihydrofolate reductase transcriptional units on the same plasmid. After selection in medium lacking hypoxanthin, glycin, and thymidin and supplemented with 10% thoroughly dialyzed foetal calf serum, a pool of cell clones was obtained that produced 110 mU/ml factor VIII:C activity as measured by the Coatest method. Selection for gene amplification by cultivation several weeks in 20 mM methotrexate yielded a pool of resistant cell clones that produced 1.5 U/ml factor VIII:C in roller bottles.

EXAMPLE 3

Biochemical Characterisation of factor VIII:R3, factor VIII:R4 and factor VIII:R5.

Factor VIII:R3, factor VIII:R4 and factor VIII:R5 produced by their respective amplified CHO-DG44 cell-line pools as described in Example 2, were examined for biochemical characteristics. Purification of the material from culture medium was performed by immunoaffinity chromatography with the use of monoclonal antibodies directed against Factor VIII followed by an ion-exchange chromatography step. The specific activity of the purified material obtained was in the range of 3000–4000 IU/$A_{280}$ and the ratio Factor VIII activity/Factor VIII antigen was close to 1 (activity was measured with Coatest (KABI-Pharmacia), and antigen was determined by an Elisa assay with use of monoclonal antibodies directed against the 80 kDa chain).

Figure 6:
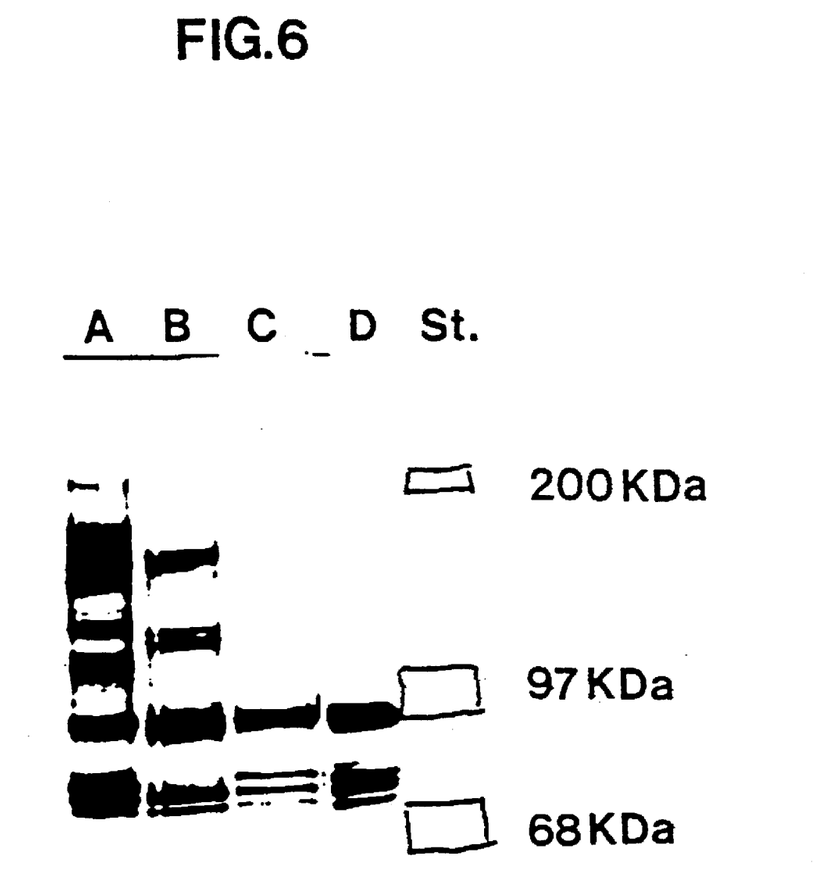
FIG. 6 is an illustration of immuno-blotting of factor VIII:R3, factor VIII:R4, factor VIII:R5, and plasma derived factor VIII after polyacrylamide gel electrophoresis in the presence of sodium dodecyl sulfate. Lane A: plasma factor VIII. Lane B: factor VIII:R3. Lane C: factor VIII:R4. Lane D: factor VIII:R5. Lane St: BRL prestained molecular weight standard, high range, from Bethesda research laboratories.

The purified factor VIII:R3, factor VIII:R4 and factor VIII:R5 were submitted to SDS-polyacrylamide gel electrophoresis (SDS-PAGE) and Western blot analysis. The SDS-PAGE was carried out according to Laemmli (1970; Nature 227, 680–685). Rabbit polyclonal anti-human factor VIII antibodies described previously (Andersson, L.-O., et al. (1986), Proc. Natl. Acad. Sci. U.S.A., 83,2979–2983) were used for the Western blot analysis essentially performed as described by Towbin, H., et al. (1979, Proc. Natl. Acad. Sci. U.S.A., 76, 4350–4354). The results are shown in FIG. 6. Lane A: plasma factor VIII, containing an 80 kDa light chain and heavy chains ranging from 200 kDa to 90 kDa. Lane B: factor VIII:R3. Lane C: factor VIII:R4. Lane D: factor VIII:R5. Factor VIII:R3 shows bands at 80 kDa, 90 kDa, 130 kDa, and 170 kDa. The 80 kDa and 90 kDa bands were found in the same position on the gel as the 80 kDa 90 kDa peptides representing the smallest biologically active complex of plasma factor VIII. The 170 kDa band probably represents the non-processed primary translation product and the band at 130 kDa an incorrectly processed form of factor VIII:R3. Thus, non-authentic polypeptide chains have also been obtained in addition to the 80 kDa and 90 kDa chains. Factor VIII:R4 and factor VIII:R5 show bands at 80 kDa and 90 kDa. There were no significant amount of non-processed primary translation product (170 kDa chain) present in these materials. This means that the in vivo proteolytic processing of the primary translation product into two polypeptide chains were effective in these cases, Thus a two-chain molecule with peptide chains of molecular weights corresponding to those present in the smallest active plasma factor VIII form were obtained in both cases. Furthermore, N-terminal sequence determination with automated Edman degradation of the factor VIII:R5 showed that the amino-termini of the 90k Da and 80 kDa chains are identical to those of plasma derived 90 kDa plus 80 kDa factor VIII.

Figure 7:
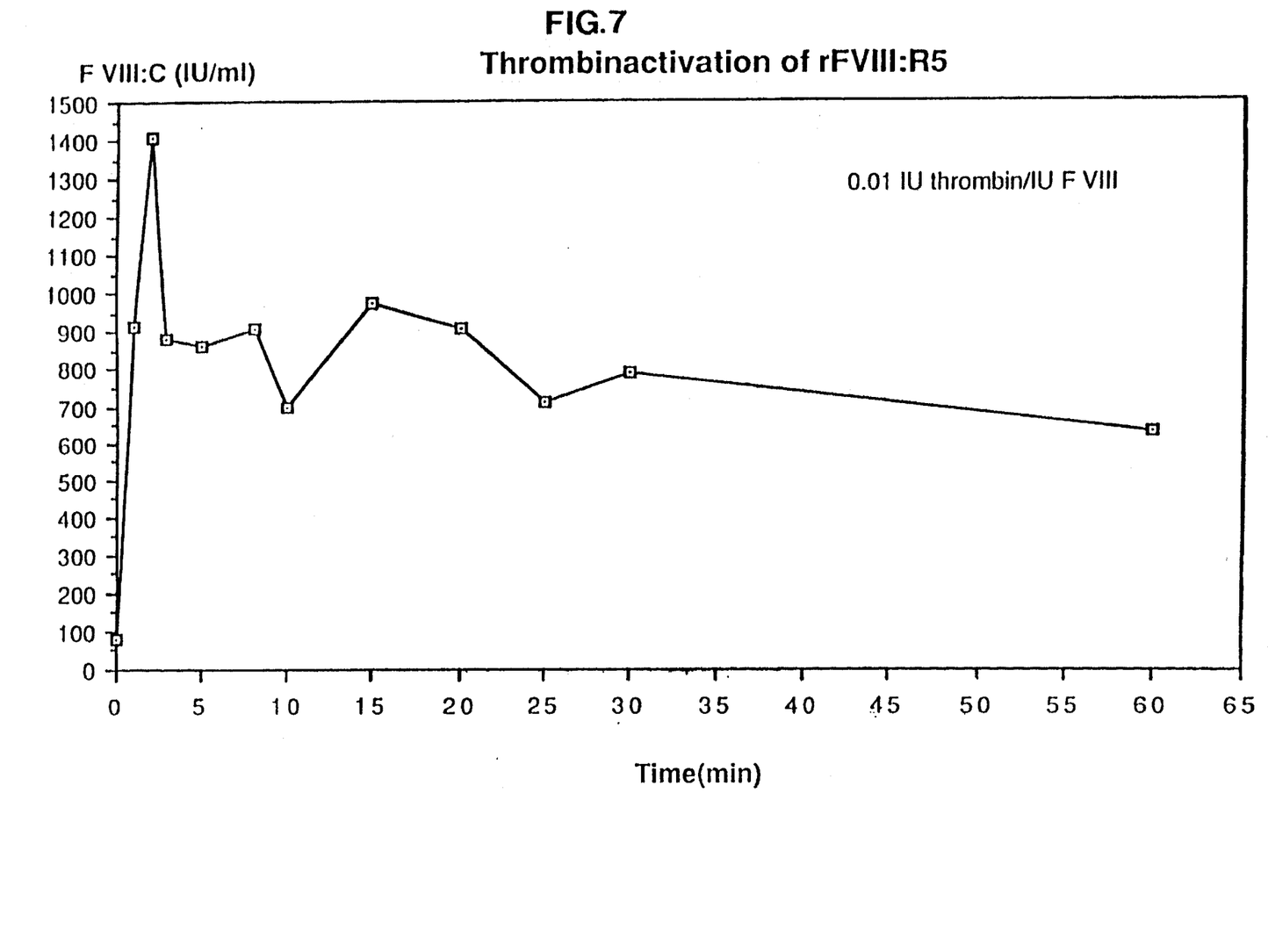
FIG. 7 shows a diagram on changes in factor VIII activity of recombinant factor VIII:R5 following incubation with human α-thrombin.
Figure 8:
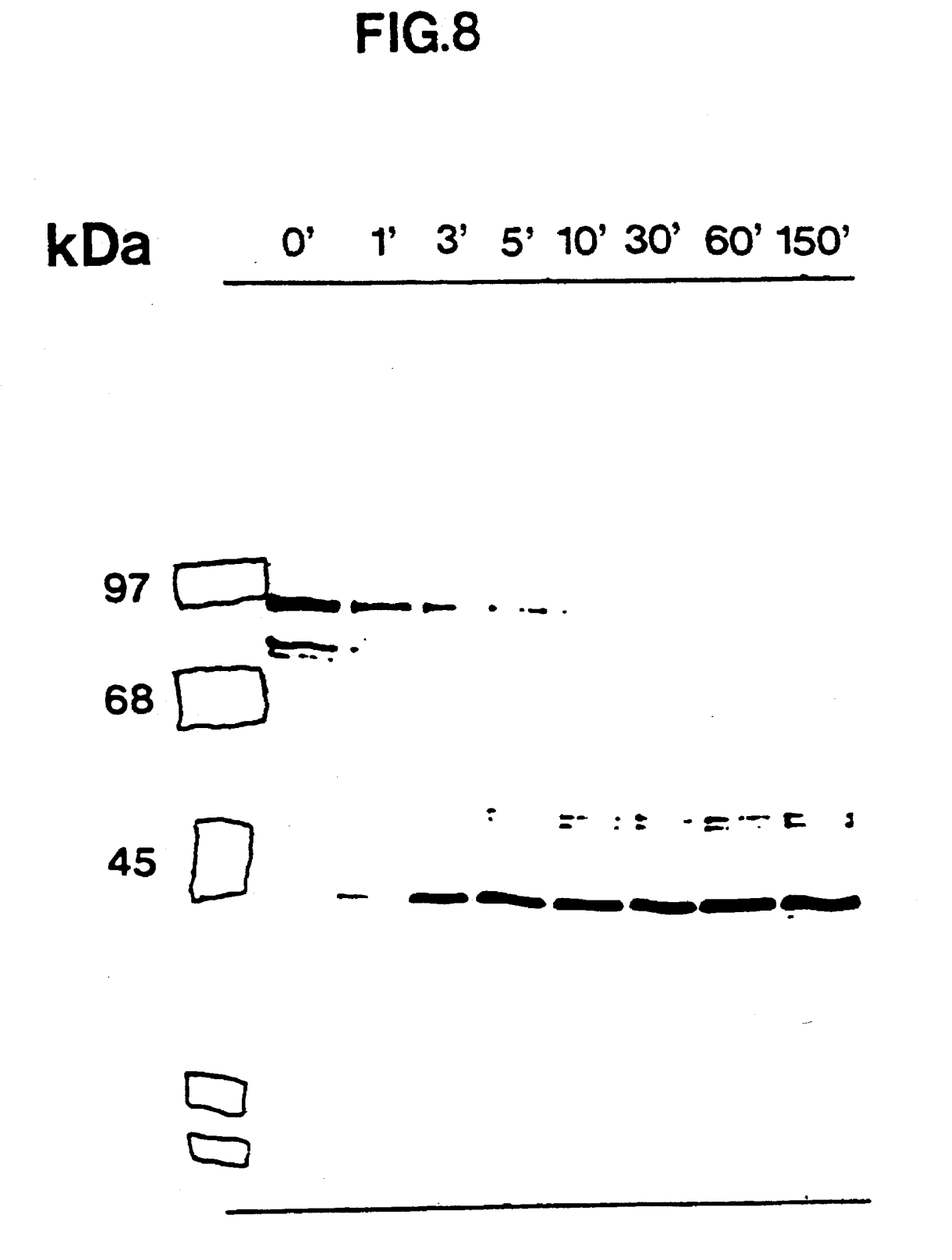
FIG. 8 illustrates changes in patterns of SDS-PAGE and immunoblotting of recombinant factor VIII:R5 following incubation with human α-thrombin (0.01 NIH units thrombin/1 IU factor VIII:C)

In FIGS. 7 and 8 are shown the activation curve and the SDS-PAGE/Western blot pattern obtained after incubation of factor VIII:R5 with thrombin (0.01 U thrombin per 1 U factor VIII was added). A one-stage clotting method (Mikaelsson, M. et al., (1983) Blood 62, 1006–1015) was used for immediate assay of samples from the reaction mixture. A 17-fold activation was obtained within two minutes, which then was followed by inactivation. Sodium dodecyl sulphate at 0.02 g/ml was added to stop the reaction in samples for analysis by SADS-PAGE/Western blot. Electrophoresis and Western blot analysis were carried out on samples, taken out at time intervals during the reaction, as described in relation to FIG. 6. The results obtained showed a molecular change of factor VIII peptides identical to that of plasma factor VIII during incubation with thrombin. Thus the 90 kDa peptide was cleaved by thrombin and a 50 kDa plus a 40 kDa peptide was formed. The 80 kDa peptide was cleaved and a 70 kDa peptide was formed. The studies with thrombin showed that factor VIII:R5 behaves as plasma factor VIII in the interaction with this enzyme. This feature is regarded to be essential for biological activity in vivo.

The interaction of Factor VIII:R5 with human von Willebrand factor was studied with the use of size exclusion chromatography on Sepharose CL-6B. Ten (10) IU of Factor VIII:R5 was incubated with 30 U purified human von Willebrand factor at 37° C. for 20 minutes. The incubation mixture was then applied on a column packed with Sepharose CL-6B. All material with Factor VIII activity eluted in the void volume with von Willebrand factor. When Factor VIII:R5 with no added von Willebrand factor was applied on the column, material with Factor VIII activity eluted only in the inner fractions at a position where also the 90 kDa-80 kDa form of plasma Factor VIII eluted. This result show that Factor VIII:R5 has the capacity to bind to von Willebrand factor, which is a property necessary for good in vivo survival (Brinkhous, K. M., et al. (1985) Proc. Natl. Acad. Sci. U.S.A. 82, 8752–8756).

The factor VIII derivatives of the present invention have been deposited with Deutsche Sammlung von Mikroorganismen und Zellkulturen on Mar. 13, 1991. Accordingly, factor VIII:R3 has been given the deposition number DSM 6415, factor VIII:R4 has been given the deposition number DSM 6417, and factor VIII:R5 has been given the deposition number DSM 6416.

We claim:

1. A DNA sequence coding for a biologically active recombinant human factor VIII derivative, comprising a first DNA segment coding for the amino acids 1 through 740 of human factor VIII and a second DNA segment coding for the amino acids 1649 through 2332 of human factor VIII, said segments being interconnected by a linker DNA segment coding for a linker peptide of at least 3 amino acid residues and up to about 10 amino acid residues which are selected from lysine and arginine.

2. A DNA sequence according to claim 1, wherein said linker DNA segment codes for 3 or 4 amino acid residues.

3. A DNA sequence according to claim 2, wherein said linker DNA segment codes for 3 or 4 amino acid residues, the amino acid residue preceding Glu-1649 being arginine.

4. A DNA sequence according to claim 2, wherein all amino acid residues of said linker are arginine.

5. A DNA sequence according to claim 2, wherein said linker DNA segment codes for 3 or 4 amino acid residues constituted by arginine.

6. A DNA sequence according to claim 1, wherein said linker DNA segment codes for 3 or 4 amino acid residues, the amino acid residue preceding Glu-1649 being arginine.

7. A DNA sequence according to claim 6, wherein all amino acid residues of said linker are arginine.

8. A DNA sequence according to claim 1, wherein all amino acid residues of said linker are arginine.

9. A DNA sequence according to claim 1, wherein said linker DNA segment codes for 3 or 4 amino acid residues constituted by arginine.

10. A process for the manufacture of a biologically active recombinant human factor VIII derivative expressed by a DNA sequence according to claim 9, comprising: cultivating an animal cell line, transformed with a recombinant expression vector containing a transcription unit comprising said DNA sequence, a transcriptional promoter, and a polyadenylation sequence, in a nutrient medium allowing expression and secretion of a human factor VIII derivative composed of two polypeptides with molecular weights of 90 kDa and 80 kDa, respectively, linked to each other by a metal ion bond; and recovering said derivative from the culture medium.

11. A recombinant expression vector containing a transcription unit comprising the DNA sequence according to claim 1, a transcriptional promoter, and a polyadenylation sequence.

12. A host cell of animal origin transformed with the recombinant expression vector of claim 7.

13. A process for the manufacture of a biologically active recombinant human factor VIII derivative expressed by a DNA sequence according to claim 1, comprising cultivating an animal cell line transformed with a recombinant expression vector containing a transcription unit comprising said DNA sequence, a transcriptional promoter, and a polyadenylation sequence in a nutrient medium allowing expression and secretion of a human factor VIII derivative composed of two polypeptides with molecular weights of 90 kDa and 80 kDa, respectively, linked to each other by a metal ion bond; and recovering said derivative from the culture medium.

* * * * *